US005527306A

United States Patent [19]

Haining

[11] Patent Number: 5,527,306

[45] Date of Patent: Jun. 18, 1996

[54] VIAL ADAPTER

[76] Inventor: Michael L. Haining, 6731 Ashmore, Houston, Tex. 77069

[21] Appl. No.: 229,190

[22] Filed: Apr. 18, 1994

[51] Int. Cl.[6] .......... A61B 19/00

[52] U.S. Cl. .......... 604/411; 604/414

[58] Field of Search .......... 604/280, 283, 604/264, 257, 239, 240, 407, 411, 415, 213, 90, 243, 68, 414; 215/3; 141/391

[56] References Cited

U.S. PATENT DOCUMENTS

| | | | |
|---|---|---|---|
| 3,206,073 | 9/1965 | Scislowicz | 604/414 |
| 4,409,990 | 10/1983 | Mileikowsky | 604/280 |
| 4,412,832 | 11/1983 | Kling et al. | 604/280 |
| 4,441,621 | 4/1984 | Matukura et al. | 215/247 |
| 4,518,385 | 3/1985 | Lindmayer et al. | 604/68 |
| 5,211,638 | 5/1993 | Dudar et al. | 604/283 |
| 5,242,423 | 9/1993 | Goodsir et al. | 604/243 |
| 5,269,771 | 12/1993 | Thomas et al. | 604/213 |
| 5,279,583 | 1/1994 | Shober, Jr. et al. | 604/198 |
| 5,298,024 | 3/1994 | Richmond | 604/90 |

*Primary Examiner*—Corrine M. McDermott
*Assistant Examiner*—N. Kent Gring
*Attorney, Agent, or Firm*—Richard L. Moseley

[57] ABSTRACT

An adapter for a medicinal vial is provided which includes a conical spike on one end for insertion through the rubber puncture pad in the lid of a medicinal vial. The end opposite the spike is provided with a standard male luer connection and pre-slit rubber cover. The male luer connector of a syringe may be easily passed through the slit to withdraw liquid from the vial by action of the piston. The rubber cover keeps the end of the adapter sealed. In one embodiment the adapter includes a valve in the upper portion to seal the end which opens in response to the attachment of a syringe.

4 Claims, 3 Drawing Sheets

VIAL ADAPTER

BACKGROUND OF THE INVENTION

1. Field of the Invention

The present invention relates to medical vials which contain medicines. More particularly the invention relates to medical vials which have rubber puncture pads in the lids for insertion of cannulae of hypodermic syringes for retraction of the medicine contained therein. More particularly the invention relates to an adapter for insertion through the rubber puncture pad which allows the use of a syringe without using a cannula.

2. Related Information

The advent of the AIDS virus has focused attention on diseases which are transmitted by contact with contaminated blood. One source of contaminated blood is the exposed cannula on a hypodermic syringe, catheters and the like. Many devices are now available on the market to reduce the likelihood of such contact. More particularly there have been devices for retracting the needles of hypodermic syringes into the barrel after use as exemplified in my own U.S. Pat. Nos. 4,790,822; 4,950,251 and 5,152,750. Additionally the insertion cannula of a catheter has also been made retractable as in my U.S. Pat. No. 5,019,049. A blood drawing device with a retractable needle is disclosed in U.S. Pat. No. 5,070,885.

Medications are often shipped in vials or bottles which have a cover which includes a rubber puncture pad for insertion of a cannula. Generally the cannula is inserted through the puncture pad and the fluid medicine withdrawn up into the barrel of a piston syringe by action of the piston. As long as the medicine is to be injected into a patient directly utilizing the cannula the practice cannot be modified. However, often the medication is to be injected into a solution being administered intravenously. In the case of the intravenous administration the cannula is usually inserted through another puncture pad on a Y connection or "piggy back" included in the intravenous injection apparatus. Needleless systems are now being developed wherein the syringe itself may be directly attached to the Y connector. See for example my own patent application Ser. No. 08/157,306 filed Nov. 26, 1993.

The one remaining part of the needleless system is a method and apparatus for transferring the liquid in the vial to the syringe without a cannula. It is a feature of the present invention that the transfer of liquid from a vial having a rubber puncture pad to a piston syringe may be effected without the use of a cannula. It is a further feature that when used in combination with my earlier invention disclosed in U.S. patent application Ser. No. 08/157,306 that the liquid may be transferred from the vial to the patient without the use of a sharp cannula.

SUMMARY OF THE INVENTION

The present invention comprises an adapter which includes a conical spike on one end for insertion through the rubber puncture pad in the lid of a medicinal vial. The end opposite the spike is provided with a standard male luer connection and pre-slit rubber cover. The male luer connector of a syringe may be easily passed through the slit to withdraw liquid from the vial by action of the piston. The rubber cover keeps the end of the adapter sealed.

In one embodiment the adapter includes a valve in the upper portion to seal the end. When the valve is used to seal the adapter the rubber cover can be substantially thinner allowing for easier insertion of the male luer.

In some embodiments the adapter has gripping surfaces to grip the rubber puncture pad on the vial lid on either side. The gripping of the adapter prevents rotational movement of the adapter when a syringe is threaded onto the luer.

DESCRIPTION OF THE PREFERRED EMBODIMENT

For a detailed description of the preferred embodiment the reader is referred to the appended figures in which like components are given like numerals for ease of reference.

Figure 1:
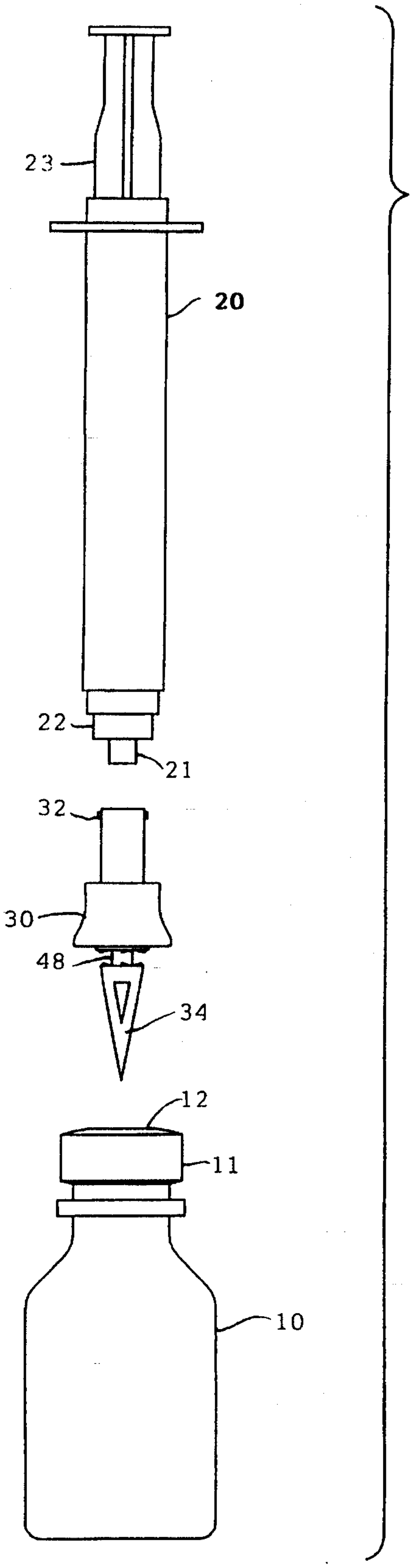
FIG. 1 is a plan view showing the relationship of the adapter of the present invention, syringe and vial.

Referring first to FIG. 1 there is shown the arrangement of the adapter of the present invention in relation to a medicinal vial and piston syringe. The adapter 30 is shown to have a conical spike 34 on the lower end which may inserted through the puncture pad 12 in the lid 11 of a medicinal vial 10. The spike 34 is separated from the main body 33 by a narrow neck 48 the length of which is approximately the thickness of the rubber puncture pad 12. The upper end of the adapter is provided with standard male luer connectors 32. The extension 21 on the lower end of piston syringe 20 may be passed through the pre-slit in the rubber pad (not shown) on the upper end of the adapter 30 and the male luer connectors 21 may be engaged with the female luer connection 22 on lower end of syringe 20. The liquid may then be withdrawn into the syringe by action of the piston 23.

Figure 2:
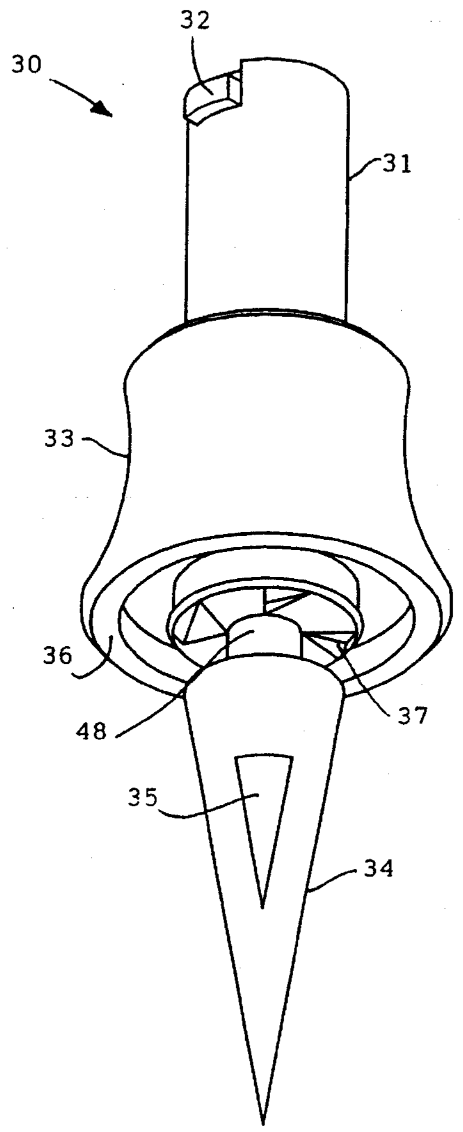
FIG. 2 is an isometric view of the vial adapter.
Figure 3:
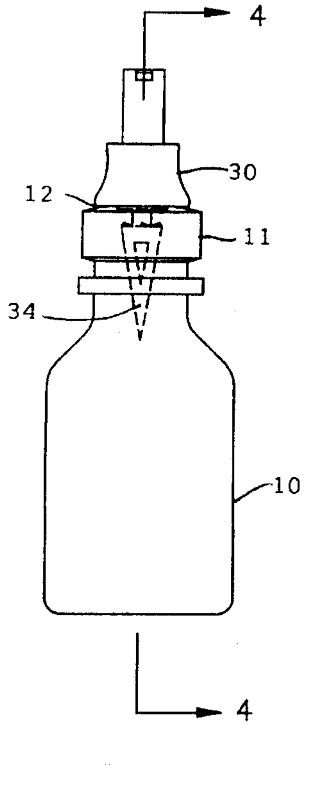
FIG. 3 is a side view showing the adapter mounted on a medicinal vial.
Figure 4:
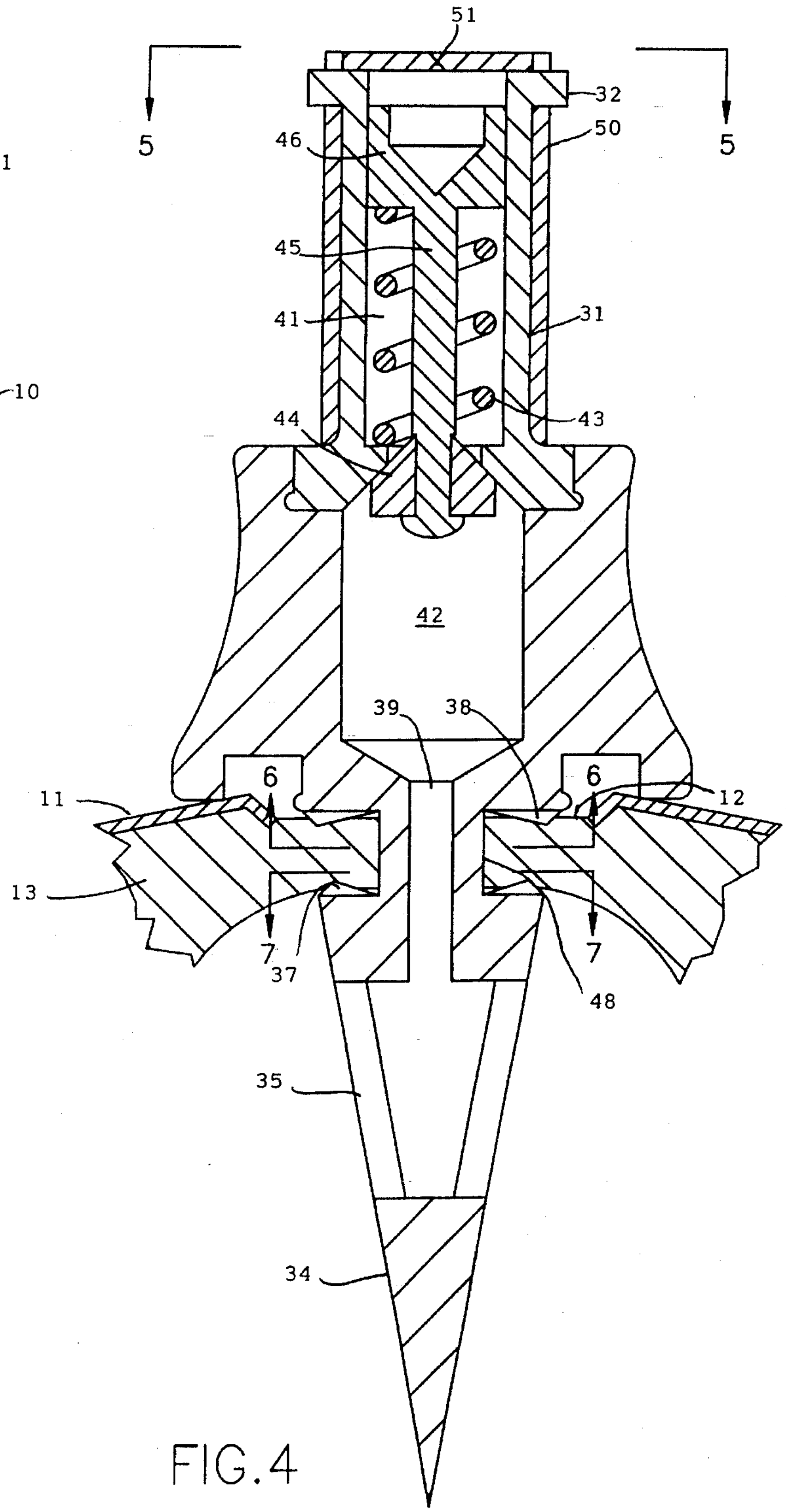
FIG. 4 is a elevational view in cross section taken along line 4—4 in FIG. 3.
Figure 5:
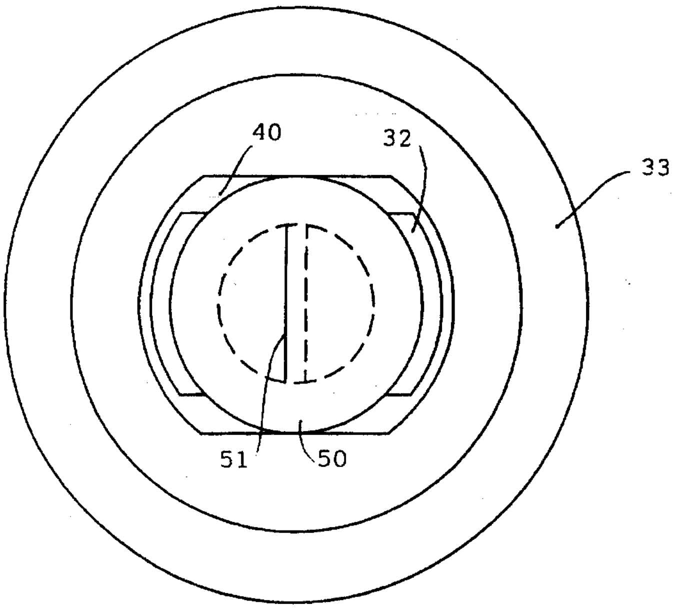
FIG. 5 is a view taken along line 5—5 of FIG. 4.
Figure 6:
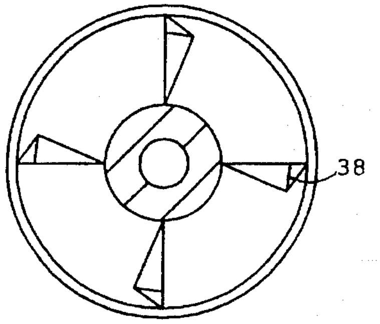
FIG. 6 is a view taken along line 6—6 of FIG. 4 showing the gripping surfaces which grip the upper surface of the rubber puncture pad.
Figure 7:
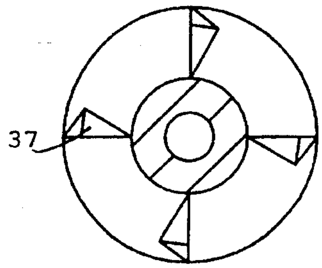
FIG. 7 is a view taken along line 7—7 of FIG. 4 showing the gripping surfaces which grip the under surface of the rubber puncture pad.

FIG. 2 shows more detail of the outside of adapter 30. The upper barrel 31 of the adapter is seen to be cylindrical and has luer connectors at the end. The middle portion of the adapter is seen to comprise a bell shaped base 33 having a flat annular surface 36 on the under side. Concentric with and inside of annular surface 36 is upper gripping surface 37. Coaxial with and extending from upper gripping surface is a narrow neck 48 to which is connected a conical spike 34 having openings 35.

Referring now to FIG.'s 3–8 more detail of the adapter as mounted 30 mounted on a vial 10 is shown. In the embodiment shown the upper barrel 31 is seen to have an upper chamber 47 containing a valve made up of a stem 45 having a seat 44 at the lower end and an actuator 46 at the upper end. A spring 43 surrounds the stem 45 and provides an upward force to bias the seat 44 in the closed position. The actuator 46 is activated by pressure from the extension 21 (FIG. 1) on syringe 20 when syringe is threaded onto luer connectors 32.

Directly below upper chamber 47 is lower chamber 42 with liquid passageway 39 leading to openings 35 in spike 34. The barrel 31 is shown to be covered with rubber cover 50 having a slit 51 in the upper surface. The male luer connectors are passed through openings in cover 50. The slit is made at an angle in the rubber cover to provide a sealing surface for the elastic rubber. It should be understood that the thinner the rubber material the larger the angle to provide more surface for elastic sealing.

The bell shaped base 33 provides a relatively large area at the lower end so that annular surface 36 will rest on the upper surface of cap 11. The large diameter of under side of bell shaped base 33 provides for stability when attached to lid 11.

Figure 8:
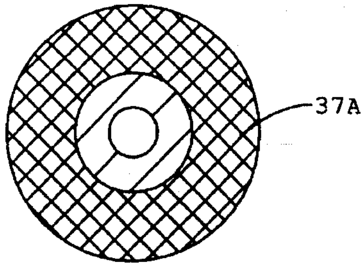
FIG. 8 is a view showing an alternate gripping surface for either the upper or lower part of the adapter.

The under surface of bell shaped base includes grippers 38 which grip the upper surface of the rubber puncture pad 12. The upper surface of the conical spike also includes similar grippers 37. The grippers 37 and 38 are positioned so that they grip in the opposite directions providing rotational stability for the adapter during threaded engagement of the syringe. The narrow neck 48 is shown to be approximately the length of the thickness of the rubber puncture pad 12 so that grippers 37 and 38 are forced against the puncture pad. In lieu of the grippers 37 and 38 a simpler knurled surface as shown in FIG. 8 may be used.

The invention claimed is:

1. An adapter for connecting a syringe directly to a medical vial having a rubber puncture pad in the lid, comprising:

a hollow body having an upper end, a lower end and a base, said hollow body being open at the upper end;

a normally closed valve in said body that opens in response to the attachment of a syringe;

a conical spike, said conical spike having a spike base, and being connected to said body at the lower end by a narrow neck having a smaller diameter than said spike base thereby defining a upper surface on said spike, said neck having a length of approximately the thickness of said puncture pad such that the upper surface of said conical spike fits snugly against the lower surface of a puncture pad when said adapter is mounted on a vial;

the upper end of said body comprising a male luer connection; and a pre-slit rubber cover over said open upper end.

2. The adapter according to claim 1 wherein said lower end has an underside and further comprising gripping surfaces on said underside of said body and the upper surface of said spike.

3. The adapter according to claim 1 wherein said body comprises an upper cylindrical barrel portion connected a lower bell shaped base.

4. An adapter for connecting a syringe directly to a medical vial having a rubber puncture pad in the lid, comprising:

a hollow body open at the upper end and having an upper end, a lower end and an upper cylindrical barrel connected to a lower bell shaped base, said base having an underside;

a normally closed valve contained within said barrel that opens in response to the attachment of a syringe;

a conical spike, said spike having an upper surface and being attached to the under surface of said base by a narrow neck, the length of said neck being approximately equal to the thickness of said rubber puncture pad such that said upper surface of said conical spike fits snugly against the lower surface of a puncture pad when said adapter is mounted on a vial;

gripping surfaces on said under side of said base and on said upper surface of said spike;

said upper end of said barrel comprising a male luer connection; and a pre-slit rubber cover over said open upper end.

* * * * *